US008003090B2

(12) United States Patent
Dreano et al.

(10) Patent No.: US 8,003,090 B2
(45) Date of Patent: *Aug. 23, 2011

(54) METHOD FOR INHIBITING A MICROVASCULAR COMPLICATION BY ADMINISTERING IL-6

(75) Inventors: Michel Dreano, Collonges sous Salève (FR); Pierre-Alain Vitte, Cranves-Sales (FR); Norman Cameron, Aberdeen (GB); Mary A. Cotter, Aberdeen (GB)

(73) Assignee: Merck Serono SA, Coinsins, Vaud (CH)

( * ) Notice: Subject to any disclaimer, the term of this patent is extended or adjusted under 35 U.S.C. 154(b) by 132 days.

This patent is subject to a terminal disclaimer.

(21) Appl. No.: 11/661,214

(22) PCT Filed: Aug. 30, 2005

(86) PCT No.: PCT/IL2005/000928
§ 371 (c)(1),
(2), (4) Date: Sep. 10, 2007

(87) PCT Pub. No.: WO2006/025057
PCT Pub. Date: Mar. 9, 2006

(65) Prior Publication Data
US 2008/0107621 A1    May 8, 2008

(30) Foreign Application Priority Data
Sep. 1, 2004   (IL) .......................... 163856

(51) Int. Cl.
*A61K 38/19*   (2006.01)
*A61K 38/20*   (2006.01)
(52) U.S. Cl. ...................... 424/85.2; 514/1.1

(58) Field of Classification Search .................. None
See application file for complete search history.

(56) References Cited

U.S. PATENT DOCUMENTS
2008/0193409 A1   8/2008   Dreano et al.

FOREIGN PATENT DOCUMENTS
WO    WO 03/033015       *  4/2003
WO    2005105135 A1   11/2005

OTHER PUBLICATIONS

Callizot et al., Cancer Chemother. Pharmacol. 62:995-1007 (2008).
Bursell et al., Curr. Eye Res. 11(4):287-295 (1995).
Akibo et al., Diabetes 52:829-837 (2003).
Ishii et al., Science 272:728-731 (1996).
Mayhan, Brain Research 580:297-302 (1992).
Keegam et al., Free Rad. Biol. Med. 27:536-543 (1999).
Tribe et al., Diabetologia 41:34-39 (1998).
Cameron et al., Diabetologia 35:1011-1019 (1992).
Pelligrino et al, NeuroReport 5:417-420 (1994).
Edgley et al., Am. J. Physiol. Regul. Integr. Comp. Physiol. 295:R829-R839 (2008).
Bell et al., J. Am. Soc. Nephrol. 17:2184-2192 (2006).
De Vriese et al., Diabetologia 43:1116-1125 (2000).
Hashimoto et al., Diabetes 38:1109-1113 (1989).
Dorland's Illustrated Medical Dictionary, 29th edition, W.B. Saunders Company, Philadelphia, 2000, pp. 1187, 1212 and 1567.

* cited by examiner

*Primary Examiner* — Prema Mertz
(74) *Attorney, Agent, or Firm* — Browdy and Neimark, PLLC

(57) ABSTRACT

The present invention relates to the use of IL-6 or a fragment, variant, fusion protein, functional derivative or salt thereof in microvascular complications.

17 Claims, 4 Drawing Sheets

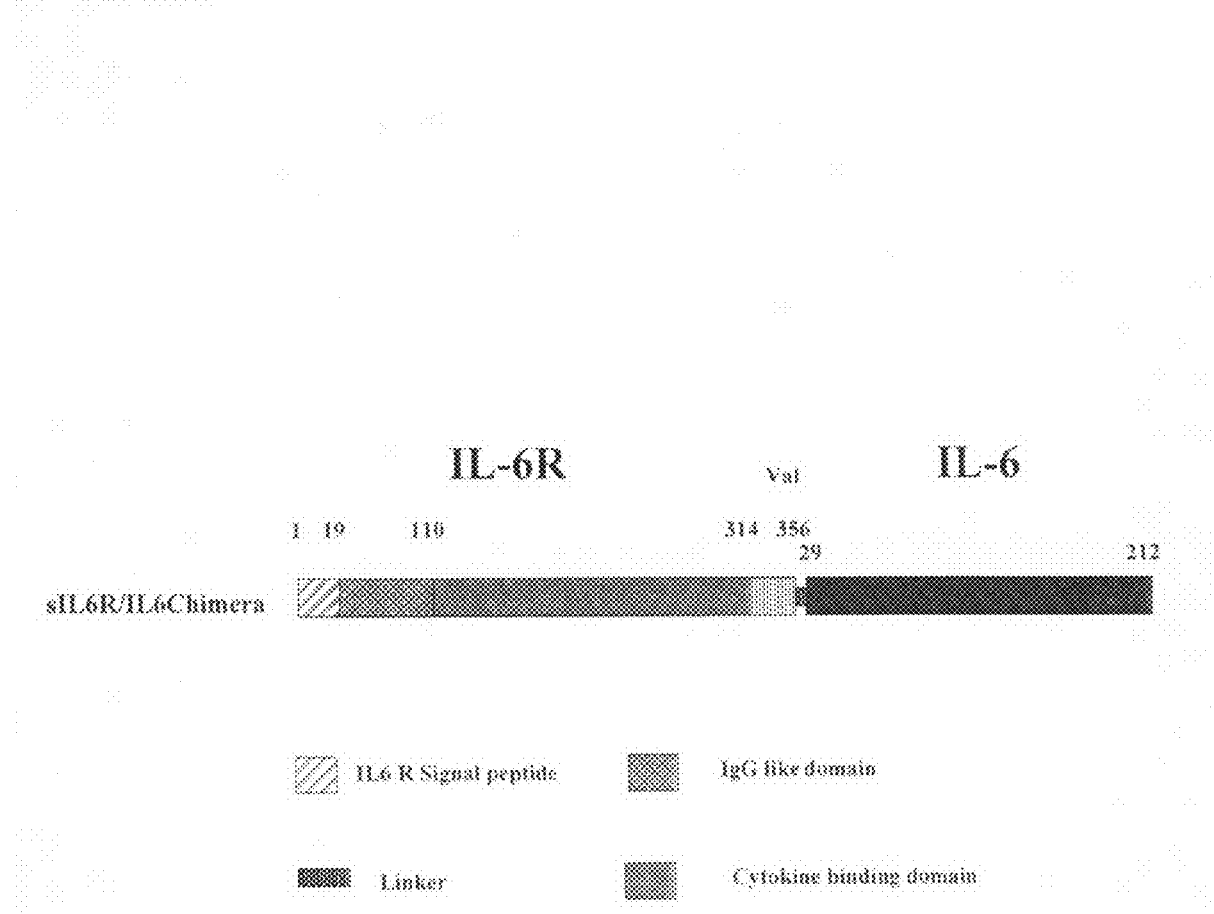

METHOD FOR INHIBITING A MICROVASCULAR COMPLICATION BY ADMINISTERING IL-6

FIELD OF THE INVENTION

The present invention is in the field of microvascular complications. In particular, it relates to the use of IL-6 or a fragment, variant, fusion protein, functional derivative or salt thereof in microvascular complications.

BACKGROUND OF THE INVENTION

Diabetes mellitus is a disorder of carbohydrate metabolism, i.e. a syndrome characterized by hyperglycemia resulting from absolute or relative impairment in insulin secretion and/or insulin action.

Classification of Diabetes mellitus is based on the one adopted by the National Diabetes Data Group and WHO. Previously, it was based on age at onset, duration, and complications of the disease. Gestational diabetes mellitus is carbohydrate intolerance of variable severity with onset or first recognition during the current pregnancy. Patients with type I diabetes mellitus (DM), also known as insulin-dependent DM (IDDM) or juvenile-onset diabetes, may develop diabetic ketoacidosis (DKA). Patients with type II DM, also known as non-insulin-dependent DM (NIDDM), may develop nonketotic hyperglycemic-hyperosmolar coma (NKHHC). Common late microvascular complications include retinopathy, nephropathy, and peripheral and autonomic neuropathies. The most important clinical sequel of sensory loss is foot ulceration, the most common cause of hospital admission in diabetic patients and the leading cause of non-traumatic lower limb amputations (Boulton 1997, Jude 1999 and Cameron 2001). Macrovascular complications include atherosclerotic coronary and peripheral arterial disease.

Type I diabetes mellitus: Although it may occur at any age, type I diabetes mellitus most commonly develops in childhood or adolescence and is the predominant type of DM diagnosed before age 30. This type of diabetes accounts for 10 to 15% of all cases of DM and is characterized clinically by hyperglycemia and a propensity to diabetic ketoacidosis. The pancreas produces little or no insulin.

About 80% of patients with type I DM have specific HLA phenotypes associated with detectable serum islet cell cytoplasmic antibodies and islet cell surface antibodies (antibodies to glutamic acid decarboxylase and to insulin are found in a similar proportion of cases).

In these patients, type I DM results from a genetically susceptible, immune-mediated, selective destruction of >90% of their insulin-secreting cells. Their pancreatic islets exhibit insulitis, which is characterized by an infiltration of T lymphocytes accompanied by macrophages and B-lymphocytes and by the loss of most of the beta-cells, without involvement of the glucagon-secreting alpha-cells. The antibodies present at diagnosis usually become undetectable after a few years. They may be primarily a response to beta-cell destruction, but some are cytotoxic for beta-cells and may contribute to their loss. The clinical onset of type I DM may occur in some patients years after the insidious onset of the underlying autoimmune process. Screening for these antibodies is included in numerous ongoing preventive studies.

Type II diabetes mellitus: Type II DM is usually the type of diabetes diagnosed in patients >30 years, but it also occurs in children and adolescents. It is characterized clinically by hyperglycemia and insulin resistance. Diabetic ketoacidosis is rare. Although most patients are treated with diet, exercise, and oral drugs, some patients intermittently or persistently require insulin to control symptomatic hyperglycemia and prevent nonketotic hyperglycemic-hyperosmolar coma. The concordance rate for type II DM in monozygotic twins is >90%. Type II DM is commonly associated with obesity, especially of the upper body (visceral/abdominal), and often present after a period of weight gain. Impaired glucose tolerance associated with aging is closely correlated with the typical weight gain. Type II DM patients with visceral/abdominal obesity may have normal glucose levels after losing weight.

Type II DM is a heterogeneous group of disorders in which hyperglycemia results from both an impaired insulin secretory response to glucose and decreased insulin effectiveness in stimulating glucose uptake by skeletal muscle and in restraining hepatic glucose production (insulin resistance). However, insulin resistance is common, and most patients with insulin resistance will not develop diabetes, because the body compensates by adequately increasing insulin secretion. Insulin resistance in the common variety of type II DM is not the result of genetic alterations in the insulin receptor or the glucose transporter. However, genetically determined post-receptor intracellular defects likely play a role. The resulting hyperinsulinemia may lead to other common conditions, such as obesity (abdominal), hypertension, hyperlipidemia, and coronary artery disease (the syndrome of insulin resistance).

Genetic factors appear to be the major determinants for the development of type II DM, yet no association between type II DM and specific HLA phenotypes or islet cell cytoplasmic antibodies has been demonstrated. An exception is a subset of non-obese adults with detectable islet cell cytoplasmic antibodies who carry one of the HLA phenotypes and who may eventually develop type I DM.

Before diabetes develops, patients generally lose the early insulin secretory response to glucose and may secrete relatively large amounts of proinsulin. In established diabetes, although fasting plasma insulin levels may be normal or even increased in type II DM patients, glucose-stimulated insulin secretion is clearly decreased. The decreased insulin levels reduce insulin-mediated glucose uptake and fail to restrain hepatic glucose production.

Hyperglycemia may not only be a consequence but also a cause of further impairment in glucose tolerance in the diabetic patient (glucose toxicity) because hyperglycemia decreases insulin sensitivity and increases hepatic glucose production. Once a patient's metabolic control improves the insulin or hypoglycemic drug dose is usually lowered.

Some cases of type II DM occur in young, non-obese adolescents (maturity-onset diabetes of the young [MODY]) with an autosomal dominant inheritance. Many families with MODY have a mutation in the glucokinase gene. Impairments in insulin secretion and in hepatic glucose regulation have been demonstrated in these patients.

Insulinopathies are rare cases of DM, with the clinical characteristics of type II DM, result from the heterozygous inheritance of a defective gene, leading to secretion of insulin that does not bind normally to the insulin receptor. These patients have greatly elevated plasma immunoreactive insulin levels associated with normal plasma glucose responses to exogenous insulin.

Diabetes may also be attributed to pancreatic disease: Chronic pancreatitis; particularly in alcoholics, is frequently associated with diabetes. Such patients lose both insulin-secreting and glucagon-secreting islets. Therefore, they may be mildly hyperglycemic and sensitive to low doses of insulin. Given the lack of effective counter regulation (exogenous insulin that is unopposed by glucagon), they frequently suffer from rapid onset of hypoglycemia. In Asia, Africa, and the Caribbean, DM is commonly observed in young, severely malnourished patients with severe protein deficiency and pancreatic disease; these patients are not prone to diabetic ketoacidosis but may require insulin.

Diagnosis of diabetes mellitus: In a symptomatic patients, DM is established when the diagnostic criterion for fasting hyperglycemia is met: a plasma (or serum) glucose level of >=140 mg/dl (>=7.77 mmol/l) after an overnight fast on two occasions in an adult or child.

An oral glucose tolerance test may be helpful in diagnosing type II DM in patients whose fasting glucose is between 115 and 140 mg/dl (6.38 and 7.77 mmol/L) and in those with a clinical condition that might be related to undiagnosed DM (e.g. polyneuropathy, retinopathy).

Hyperglycemia is correlated to most of the microvascular complications of diabetes. It demonstrated a linear relationship between the levels of Hb $A_{1c}$ (see below) and the rate at which complications developed. Other studies have suggested that Hb $A_{1c}$<8% is a threshold below which most complications can be prevented. Thus, therapy for type 1 DM should try to intensify metabolic control to lower Hb $A_{1c}$ while avoiding hypoglycemic episodes. However, treatment must be individualized and, should be modified when circumstances make any risk of hypoglycemia unacceptable (e.g. in patients with a short life expectancy and in those with cerebrovascular or cardiac disease) or when the patient's risk of hypoglycemia is increased (e.g. in patients who are unreliable or who have autonomic neuropathy).

Diet to achieve weight reduction is most important in overweight patients with type II DM. If improvement in hyperglycemia is not achieved by diet, trial with an oral drug should be started.

The patient should be regularly assessed for symptoms or signs of complications, including a check of feet and pulses and sensation in the feet and legs, and a urine test for albumin. Periodic laboratory evaluation includes lipid profile, BUN (blood urea nitrogen) and serum creatinine levels, ECG, and an annual complete ophthalmologic evaluation.

Hypercholesterolemia or hypertension increases the risks for specific late complications and requires special attention and appropriate treatment. Although beta-adrenergic receptor blocking agents (3-blockers, such as propranolol) can be used safely in most diabetics, they can mask the (3-adrenergic symptoms of insulin-induced hypoglycemia and can impair the normal counter regulatory response. Thus, ACE inhibitors and calcium antagonists are often used.

Plasma glucose monitoring should be carried out by all patients, and insulin-treated patients should be taught to adjust their insulin doses accordingly. Glucose levels can be tested with easy-to-use home analyzers using a drop of fingertip blood. A spring-powered lancet is recommended to obtain the fingertip blood sample. The frequency of testing is determined individually. Insulin-treated diabetic patients ideally should test their plasma glucose daily before meals, 1 to 2 hours after meals, and at bedtime.

Most physicians periodically determine glycosylated hemoglobin (Hb $A_{1c}$) to estimate plasma glucose control during the preceding 1 to 3 months. Hb $A_{1c}$ is the stable product of non-enzymatic glycosylation of Hb by plasma glucose and is formed at rates that increase with increasing plasma glucose levels. In most laboratories, the normal Hb $A_{1c}$ level is about 6%; in poorly controlled diabetics, the level ranges from 9 to 12%. Hb $A_{1c}$ is not a specific test for diagnosing diabetes; however, elevated Hb $A_{1c}$ often indicates existing diabetes.

Another test determines the fructosamine level. Fructosamine is formed by a chemical reaction of glucose with plasma protein and reflects glucose control in the previous 1 to 3 weeks. Therefore, this assay may show a change in control before Hb $A_{1c}$ and is often helpful when intensive treatment is applied and in short-term clinical trials.

As regards insulin treatment, human insulin is often preferred in initiating insulin treatment because it is less antigenic than animal-derived varieties. However, detectable insulin antibody levels, usually very low, develop in most insulin-treated patients, including those receiving human insulin preparations.

Insulin is routinely provided in preparations containing 100 U/ml (U-100 insulin) and is injected subcutaneous with disposable insulin syringes. The ½-ml syringes are generally preferred by patients who routinely inject doses of <=50 U, because they can be read more easily and facilitate the accurate measurement of smaller doses. A multiple-dose insulin injection device (NovolinPen), commonly referred to as an insulin pen, is designed to use a cartridge containing several days' dosage.

Diabetes may be associated with other endocrine diseases. Type II DM can be secondary to Cushing's syndrome, acromegaly, pheochromocytoma, glucagonoma, primary aldosteronism, or somatostatinoma. Most of these disorders are associated with peripheral or hepatic insulin resistance. Many patients will become diabetic once insulin secretion is also decreased. The prevalence of type I DM is increased in patients with certain autoimmune endocrine diseases, e.g. Graves' disease, Hashimoto's thyroiditis, and idiopathic Addison's disease.

Diabetes may also be induced by beta-cell toxins. Streptozotocin for instance can induce experimental diabetes in rats but rarely causes diabetes in humans.

Adults with diabetes have an annual mortality of about 5.4% (double the rate for non-diabetic adults), and their life expectancy is decreased on average by 5-10 years. Although the increased death rate is mainly due to cardiovascular disease, deaths from non-cardiovascular causes are also increased. A diagnosis of diabetes immediately increases the risk of developing various clinical complications that are largely irreversible and are due to microvascular or macrovascular disease. Duration of diabetes is an important factor in the pathogenesis of complications, but other risk factors for example, hypertension, cigarette smoking, and hypercholesterolaemia interact with diabetes to affect the clinical course of microangiopathy and macroangiopathy.

One of the microvascular complications in diabetes is retinopathy. Diabetic retinopathy is a progressive disorder classified according to the presence of various clinical abnormalities. It is the commonest cause of blindness in people aged 30-69 years. Damage to the retina arises from a combination of microvascular leakage and microvascular occlusion; these changes can be visualized in detail by fluorescein angiography. A fifth of patients with newly discovered type 2 diabetes have retinopathy at the time of diagnosis. In type 1 diabetes, vision-threatening retinopathy almost never occurs in the first five years after diagnosis or before puberty. After 15 years, however, almost all patients with type 1 diabetes and two thirds of those with type 2 diabetes have background retinopathy.

Another microvascular complication in diabetes is nephropathy. Diabetic nephropathy is characterized by proteinuria >300 mg/24 h, increased blood pressure, and a progressive decline in renal function. At its most severe, diabetic nephropathy results in end stage renal disease requiring dialysis or transplantation, but in the early stages overt disease is preceded by a phase known as incipient nephropathy (or microalbuminuria), in which the urine contains trace quantities of protein (not detectable by traditional dipstick testing). Microalbuminuria is defined as an albumin excretion rate of 20-300 mg/24 h or 20-200 μg/min in a timed collection and is highly predictive of overt diabetic nephropathy, especially in type 1 diabetes.

The rate of decline in glomerular filtration rate varies widely between individuals, but antihypertensive treatment greatly slows the decline in renal function and improves survival in patients with diabetic nephropathy.

In patients with type I diabetes complicated by diabetic nephropathy, angiotensin converting enzyme inhibitors have renoprotective effects above those that can be attributed to reduced blood pressure; they are beneficial even in normotensive patients and ameliorate other associated microvascular complications such as retinopathy. In patients with type 2 diabetes, achieving good blood pressure control (which often requires combination therapy) is more important than the choice of antihypertensive drug, although angiotensin converting enzyme inhibitors are used as first line treatment.

Another microvascular complication in diabetes is polyneuropathy, being the major cause for foot ulcers and joint problems, which are important causes of morbidity in diabetes mellitus. In diabetic polyneuropathy, the sensory denervation impairs the perception of trauma from such common causes as ill-fitting shoes or pebbles. Alterations in proprioception lead to an abnormal pattern of weight bearing and sometimes to the development of Charcot's joints.

Patients with infected foot ulcers frequently feel no pain because of neuropathy and have no systemic symptoms until late in a neglected course. Deep ulcers and particularly ulcers associated with any detectable cellulites require immediate hospitalization, since systemic toxicity and permanent disability may develop. Early surgical debridement is an essential part of management, but amputation is sometimes necessary.

Interleukin-6 (IL-6) is a multifunctional cytokine produced and secreted by several different cell types. This pleiotropic cytokine plays a central role in cell defense mechanisms including the immune response, acute phase response and hematopoiesis. IL-6 is a 20 to 26 kDa glycoprotein having 185 amino acids that has been cloned previously (May et al, (1986); Zilberstein et al, (1986); Hirano et al, (1986)). IL-6 has previously been referred to as B cell stimulatory factor 2 (BSF-2), interferon-beta 2 and hepatocyte stimulatory factor. IL-6 is secreted by a number of different tissues including the liver, spleen, and bone marrow and by a variety of cell types including monocytes, fibroblasts, endothelial, B- and T-cells. IL-6 is activated at the transcriptional level by a variety of signals including viruses, double stranded RNA, bacteria and bacterial lipopolysaccarides, and inflammatory cytokines such as IL-1 and TNF.

The biological activities of IL-6 are mediated by a membrane receptor system comprising two different proteins one named IL-6 receptor or gp80 and the other gp130 (reviewed by Hirano et al, 1994). gp130 is a transmembrane glycoprotein with a length of 918 amino acids, including an intracellular domain of 277 amino acids, is a subunit constituent of several cytokine receptors, including those for IL-6, IL-11, LIF, Oncostatin M, CNTF (ciliary neurotrophic factor), CT-1. IL-6 being the prototype of the cytokines acting through gp130, this cytokine family is also called "IL-6 type cytokines".

gp130 participates in the formation of high-affinity receptors for these cytokines by binding to low affinity receptor chains. Accordingly, gp130 has been called also an "affinity converter". Ligand binding to a cytokine receptor leads to the dimerization of gp130 (shown for the IL-6 receptor) or heterodimerization (shown for LIF, Oncostatin M, and CNTF receptors) with a gp130-related protein known as the LIFR-beta subunit. Binding of the respective ligands is associated with the activation/association of a family of tyrosine kinases known as Janus kinases (JAKs), as the first step of intracellular signal transduction. Intracellular signaling processes include tyrosine phosphorylation and activation factors called STATs (signal transducer and activator of transcription).

The human gp130 gene product appears to be homologous to two distinct chromosomal loci on chromosomes 5 and 17. The presence of two distinct gp130 gene sequences is restricted to primates and is not found in other vertebrates.

It has been shown that the signaling activities of IL-6, IL-11, CNTF, Oncostatin M and LIF can be blocked specifically by different monoclonal antibodies directed against gp130. In addition to this, monoclonal antibodies, which directly activate gp130 independently of the presence of cytokines or their receptors have been found.

Other monoclonal antibodies directed against gp130 have been shown to inhibit IL-6-mediated functions. Soluble forms of gp130 (sgp130) with molecular masses of 90 and 110 Kda have been found in human serum. They can inhibit biological functions of those cytokines utilizing receptor systems with gp130 as a component.

Soluble forms of IL-6R gp80 (sIL-6R), corresponding to the extracellular domain of gp80, are natural products of the human body found as glycoproteins in blood and in urine (Novick et al, 1990, 1992). An exceptional property of sIL-6R molecules is that they act as potent agonists of IL-6 on many cell types including human cells (Taga et al, 1989; Novick et al, 1992). Even without the intracytoplasmic domain of gp80, sIL-6R is still capable of triggering the dimerization of gp130 in response to IL-6, which in turn mediates the subsequent IL-6-specific signal transduction and biological effects (Muralcami et al, 1993). sIL-6R has two types of interaction with gp130 both of which are essential for the IL-6 specific biological activities (Halimi et al., 1995), and the active IL-6 receptor complex was proposed to be a hexameric structure formed by two gp130 chains, two IL-6R and two IL-6 ligands (Ward et al., 1994; Paonessa et al, 1995).

The circulating concentrations of sIL-6R (agonist) in normal subjects are relatively high and comparable to those of soluble gp130 (a natural antagonist of IL-6) of above 10 ng/ml (Corbi et al 2000 Eur J Cardiotherac Surg. 18 (1): 98-103, Disthabanchong et al. Clin Nephrol. 2002 October; 58(4):289-95). In contrast, the circulating concentrations of IL-6 are low about or below 10 pg/ml (Kado et al. 1999 Acta Diabetol. June 36 (1-2)67-72, Corbi et al 2000). Thus the effect of IL-6 administration in vivo, alone, without co-administration with sIL-6R in disease may or may not be effective and depends on the concentration of the soluble agonist/antagonist in a particular disease and in a particular location in the body.

Chimeric molecules linking the soluble IL-6 receptor and IL-6 together have been developed (Chebath et al. Eur Cytokine Netw. 1997 December; 8(4):359-65.). They have been designated IL-6R/IL-6. The chimeric IL-6R/IL-6 molecules were generated by fusing the entire coding regions of the cDNAs encoding the soluble IL-6 receptor (sIL-6R) and IL-6 (see FIG. 4). Recombinant IL-6R/IL-6 was produced in CHO cells (Chebath et al, Eur Cytokine Netw. 1997, WO99/02552). The IL-6R/IL-6 binds with a higher efficiency to the gp130 chain in vitro than does the mixture of IL-6 with sIL-6R (Kollet et al, Blood. 1999 Aug. 1; 94(3): 923-31).

IL-6 has been implicated in the pathogenesis of human inflammatory CNS diseases. Increased plasma and cerebrospinal fluid levels of IL-6 have been demonstrated in patients with multiple sclerosis (Frei et al., (1991)), for instance.

Recent experiments on the effects of IL-6 on cells of the central and peripheral nervous system indicate that IL-6 may have protective effects on neuronal cells as well as some impact on inflammatory neurodegenerative processes (Gadient and Otten, 1997, Mendel et al, 1998). IL-6 was found to prevent glutamate-induced cell death in hippocampal (Yamada et al., 1994) as well as in striatal (Toulmond et al., 1992) neurons. In transgenic mice expressing high levels of both human IL-6 and human soluble IL-6R (sIL-6-R), an accelerated nerve regeneration was observed following injury of the hypoglossal nerve as shown by retrograde labeling of the hypoglossal nuclei in the brain (Hirota et al, 1996). Furthermore, there has been some evidence that IL-6 is implied in a neurological disease, the demyelinating disorder Multiple Sclerosis (MS) (Mendel et al., 1998). Mice lacking the IL-6 gene were resistant to the experimental induction of MS. On the other hand, there have been reports indicating that IL-6 has a negative effect on neuronal survival during early post-traumatic phase after nerve injury (Fisher et al., 2001).

WO03033015 teaches the use of substances signaling through p130 such as IL-6, or an IL-6R/IL-6 chimera for the treatment and/or prevention of a specific type of neuropathy, diabetic neuropathy. In WO03033015 it was shown that the treatment with IL-6 prevented neural fibers from loss of the myelin sheath and degeneration.

As mentioned, it is well established that diabetes causes impaired nerve function. There are evidences that impaired nerve function is due to reduced nerve perfusion in diabetic patients. The latter is important for the etiology of diabetic neuropathy; several studies have shown that nerve conduction velocity deficits can be prevented or corrected by treatment with a variety of vasodilators including al-adrenoceptor antagonists, angiotensin AT1 antagonists and converting enzyme inhibitors, endothelin ETA antagonists, calcium channel blockers and nitrovasodilators [reviewed in Cameron et al 2001].

Contradictory results were published on the IL-6 vasomodulatory actions, for example, on in vivo studies reported by Baudry et al.(1996) exposure to IL-6 induced a significant dose-dependent vasoconstriction, while Minghini et al. (1998) reported on IL-6-induced vasodilatation.

As mentioned, patients with diabetes have large reduction in life expectancy and in quality of life due to diabetes-specific microvascular complications in the retina, renal glomerulus and peripheral nerve. Diabetes is the leading cause of blindness, end-stage renal disease and a variety of debilitating neuropathies. Diabetics are the fastest-growing group of renal dialysis and transplant recipients. Over 60% of diabetic patients suffer from neuropathy, which accounts for 50% of all non-traumatic amputations in the US.

Hyperglycaemia alone cannot completely explain the appearance of microvascular complications of diabetes since Intensive blood glucose control dramatically reduces microvascular complications, but does not prevent them altogether (Effect of intensive diabetes treatment on nerve conduction in the Diabetes Control and Complications Trial. Ann Neurol. 1995 December; 38(6):869-80 and Lancet 352:837-853.1998). The current optimal management of microvascular complications in diabetes can only attempt to control by controlling glycemia and then deal with the complications when they occur. Consequently, patients continue to go blind, develop renal failure, and undergo lower extremity amputations making a greater understanding of the pathogenesis of microvascular disease to enhance the development of rational therapies urgent (Cameron et al 2001).

SUMMARY OF THE INVENTION

In accordance with the present invention it has been found that the administration of IL-6 has a beneficial effect in an animal model of microvascular complication, as indicated by the IL-6-mediated correction of sciatic endoneurial blood.

Thus, the invention relates to the use of an IL-6 or a fragment, variant, fusion protein, functional derivative or salt thereof ("the substance") in the preparation of a medicament for treatment and/or prevention of microvascular complications, except of diabetic neuropathy.

In one aspect, the invention relates to the use of a targeting vector, having a DNA regulatory sequences functional in cells for enabling endogenous gene activation of IL-6, 0.15 in the manufacture of a medicament for the treatment and/or prevention of microvascular complications, except of diabetic neuropathy.

In another aspect, the invention relates to the use of a cell that has been genetically modified to produce IL-6 or a fragment, variant, fusion protein in the manufacture of a medicament for the treatment and/or prevention of a microvascular complication, except of diabetic neuropathy.

In a further aspect, the invention relates to the use of an expression vector comprising the coding sequence of an IL-6 or a fragment, variant, or fusion protein thereof in the manufacture of a medicament for the treatment and/or prevention of a microvascular complication, except of diabetic neuropathy.

The invention provides a method for treating and/or preventing a microvascular complication, except of diabetic neuropathy, comprising administering to a patient in need thereof an effective amount of IL-6 or a fragment, variant, fusion protein or salt thereof, optionally together with a pharmaceutically acceptable carrier.

In addition, the invention provides a method for the treatment and/or prevention of a microvascular complication, except of diabetic neuropathy, comprising administering to a patient in need thereof an effective amount of a targeting vector having DNA regulatory sequences functional in cells, for enabling endogenous gene activation of IL-6.

Also, the invention provides a method for the treatment and/or prevention of a microvascular complication, except of diabetic neuropathy, comprising administering to a patient in need thereof a cell that has been genetically modified to produce IL-6 or a fragment, variant, fusion protein or salt thereof in the manufacture of a medicament for the treatment and/or prevention of a microvascular complication.

The invention further provides a method for the treatment and/or prevention of a microvascular complication, except of diabetic neuropathy, comprising administering to a patient in need thereof an expression vector comprising the coding sequence of an IL-6 or a fragment, variant, or fusion protein thereof.

In one preferred embodiment, the microvascular complications are for example retinopathy, neuropathy and diabetes-independent peripheral neuropathy such as peripheral neuropathy for example due to chronic hypoxia, or due to a structural vascular disease.

In a further preferred embodiment of the invention, the microvascular complication is accompanied by hypertension.

In a further preferred embodiment of the invention, the microvascular complication is accompanied by ulcer.

In a further preferred embodiment of the invention, IL-6 is recombinant.

In a one embodiment of the invention, the substance is glycosylated at one or more sites.

In a another embodiment of the invention, the substance is not glycosylated.

In a further embodiment of the invention, the fused protein comprises an immunoglobulin (Ig) fusion.

In a further preferred embodiment of the invention, the fused protein comprises an IL6R-IL6.

In a further embodiment of the invention, the functional derivative of the substance comprises at least one moiety attached to one or more functional groups, which occur as one or more side chains on the amino acid residues.

In a further preferred embodiment of the invention, the functional derivative moiety is a polyethylene moiety.

In a further embodiment of the invention, the medicament comprises the substance in the range of 140 to 210, preferable in the range of 70 to 210 and more preferable in the range of 14 to 42 mcg.

In a further preferred embodiment of the invention, the substance is administered by subcutaneous route.

In a further preferred embodiment of the invention, the effective amount of the substance is in the range of about 2 to 3 mcg/kg, preferable 1 to 3 mcg/kg, and more preferable 0.2 to 0.6 mcg/kg.

In a further embodiment of the invention, the effective amount of the substance is about, 3 mcg/kg, 2 mcg/kg, 1 mcg/kg 0.6 mcg/kg and 0.2 mcg/kg.

In a further embodiment of the invention, the effective amount of the substance is in a range of about 140 to 210, preferably 70 to 210 and more preferably 14 to 42 mcg.

In a further embodiment of the invention, the substance is administered three times per week.

BRIEF DESCRIPTION OF THE DRAWINGS

FIG. 4 is a schematic representation of an IL6R/IL6 chimera.

DETAILED DESCRIPTION OF THE INVENTION

Figure 1:
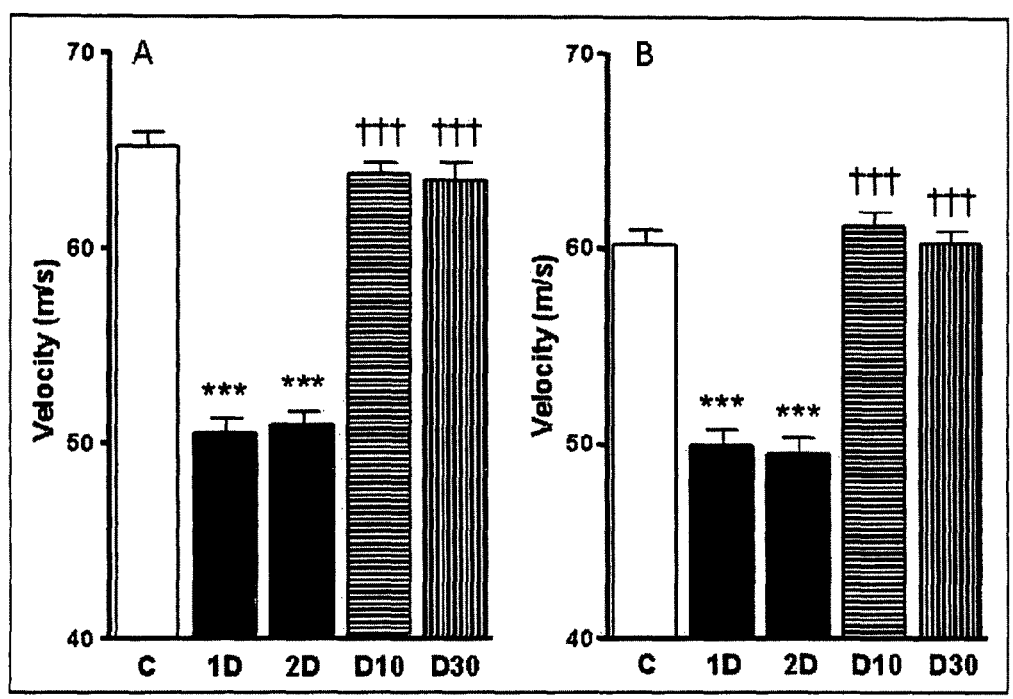
FIG. 1 shows sciatic motor (A) and saphenous sensory conduction velocity measurements. Statistics: one-way ANOVA+Newman-Keuls multiple comparison test; *** $p<0.001$ versus control group (C); ††† $p<0.001$ effects of IL-6 treatment versus diabetic (D) group. Nondiabetic control (C; n=10), 4 wk diabetes (1D; n=8-10), 8 wk diabetes (2D; n=10), 4 wk diabetes+4 week 10 mcg/kg IL6 (D10; n=10), 4 wk diabetes+4 week 30 mcg/kg IL6 (D30; n=8).

The invention is based on the finding that that the administration of IL-6 was able reduce microvascular complication in an animal model of diabetes. Therefore, the invention relates to the use of IL-6 or a fragment, variant, fusion protein, functional derivative or salt thereof ("the substance") for the preparation of a medicament for treatment and/or prevention of a microvascular complication.

The terms "treating" and "preventing" as used herein should be understood as preventing, inhibiting, attenuating, ameliorating or reversing one or more symptoms or cause(s) of microvascular complications. When "treating" microvascular complications, the substances according to the invention are given after onset of microvascular complications, "prevention" relates to administration of the substances before any signs of microvascular complications can be noted in the patient.

The term "vascular" relates to blood vessels.

The term "microvascular", pertaining to the microvasculature, relates to the portion of vasculature of the body comprising the finer vessels, sometimes described as including all vessels with an internal diameter of 100 microns or less such as arterioles, minutes arterial branches, capillaries, precapillaries, precapillary arterioles, metarterioles and venules renal tubules. The microvascullature can supply different organs e.g. renal tubules supply the kidneys, arteriole supply of the retinae, capillary found in muscle, skin, central nervous system, intestinal mucosa, renal glomeruli, pancreas, endocrine glands.

The term "complication" relates to a disease or diseases concurrent with another disease or to the concurrence of two or more diseases in the same patient.

Thus, the invention relates to microvascular complications in any disease such as e.g. diabetes, chronic obstructive pulmonary disease, a structural vascular disease, hypertension and in ulcer.

In the results found in the diabetic animal model of the present invention, it was demonstrated that blood flow impairment (and therefore hypoxia) has a central role in nerve disfunction, and that IL-6 improves the blood flow. Since, peripheral neuropathy can develop also in non-diabetic subjects suffering of chronic hypoxia, for example in a subject suffering of chronic obstructive pulmonary disease (Masson 1988 and Cameron 2001), therefore administration of the substance according to the invention is useful also in non-diabetic peropheral neuropathy.

In addition, administration of the substance according to the invention is also useful in neurological disease induced by structural vascular disease.

In a preferred embodiment of the invention, the microvascular complications are retinopathy and nephropathy.

Administration of IL-6 is especially useful in a patient having microvascular complications exhibiting high levels of IL-6 receptor in the circulation.

Hypertension in diabetic patients has been implicated as a strong risk factor for microvascular complications and therefore administration of the substance according to the invention is especially useful in diabetic and non-diabetic patients suffering of hypertension.

The fusion protein to be used according to the invention, can be preferably, an IL-6R/IL-6. An "IL-6R/IL-6" (also called "IL-6R/IL-6" or "IL-6 chimera"), as used herein, is a chimeric molecule comprising a soluble part of gp80 fused to all or a biologically active fraction of interleukin-6. The moieties of the chimeric protein can be fused directly to one another, or they can be linked by any suitable linker, such as a disulfide bridge or a polypeptide linker. The linker may be a short linker peptide, which can be as short as 1 to 3 amino acid residues in length or longer, for example, 13 or 18 amino acid residues in length. Said linker may be a tripeptide of the sequence E-F-M (Glu-Phe-Met), for example, or a 13-amino acid linker sequence comprising Glu-Phe-Gly-Ala-Gly-Leu- Val-Leu-Gly-Gly-Gln-Phe-Met introduced between the amino acid sequence of the soluble IL-6 receptor and the IL-6 sequence. Examples of IL-6 chimera are known in the art and have been described in detail e.g. in WO 99/02552 or WO 97/32891. An example for an IL-6R/IL-6 chimeric molecule, which can be used according to the invention, is depicted schematically in FIG. 4.

As used herein the term "variant" refers to analogs of IL-6 or an IL-6R/IL-6, in which one or more of the amino acid residues of the naturally occurring components of IL-6R/IL-6 are replaced by different amino acid residues, or are deleted, or one or more amino acid residues are added to the original sequence of IL-6 or an IL-6R/IL-6, without changing considerably the activity of the resulting products as compared to the original IL-6 or IL-6R/IL-6. These variants are prepared by known synthesis and/or by site-directed mutagenesis techniques, or any other known technique suitable therefore.

Variants in accordance with the present invention include proteins encoded by a nucleic acid, such as DNA or RNA, which hybridizes to the complement of the DNA or RNA encoding IL-6 or an IL-6R/IL-6 under moderately stringent or stringent conditions. The term "stringent conditions" refers to hybridization and subsequent washing conditions, which those of ordinary skill in the art conventionally refer to as "stringent". See Ausubel et al., Current Protocols in Molecular Biology, supra, Interscience, N.Y., §§6.3 and 6.4 (1987, 1992), and Sambrook et al.(Sambrook, J. C., Fritsch, E. F., and Maniatis, T. (1989) Molecular Cloning: A Laboratory Manual, Cold Spring Harbor Laboratory Press, Cold Spring Harbor, N.Y.).

Without limitation, examples of stringent conditions include washing conditions 12-20° C. below the calculated Tm of the hybrid under study in, e.g. 2×SSC and 0.5% SDS for 5 minutes, 2×SSC and 0.1% SDS for 15 minutes; 0.1×SSC and 0.5% SDS at 37° C. for 30-60 minutes and then, a 0.1× SSC and 0.5% SDS at 68° C. for 30-60 minutes. Those of ordinary skill in this art understand that stringency conditions also depend on the length of the DNA sequences, oligonucleotide probes (such as 10-40 bases) or mixed oligonucleotide probes. If mixed probes are used, it is preferable to use tetramethyl ammonium chloride (TMAC) instead of SSC, see Ausubel, supra. "Moderately stringent conditions", refer to washing conditions at lower temperatures, lower salt or lower detergent concentrations, such as in 0.2×SSC/0.1% SDS at 42° C. (Ausubel et al., 1989, supra)

Any such variant preferably has a sequence of amino acids sufficiently duplicative of that of IL-6 or an IL-6R/IL-6, such as to have substantially similar, or even better, activity as compared to IL-6 or IL-6R/IL-6.

A characteristic activity of IL-6 is its capability of binding to the gp80 portion of the IL-6 receptor, and a characteristic activity of IL-6R/IL-6 is its capability of binding to gp130. An ELISA type assay for measuring the binding of IL-6R/IL-6 to gp130 has been described in detail in example 7 on page 39 of WO 99/02552, which is fully incorporated by reference herein. The person skilled in the art will appreciate that a similar ELISA type assay can be developed for the binding of IL-6 to gp80. As long as the variant has substantial binding activity to its respective binding region of gp80 or of gp130, it can be considered to have substantially similar activity to IL-6 or IL-6R/IL-6. Thus, it can be determined whether any given variant has at least substantially the same activity as IL-6 or IL-6R/IL-6 by means of routine experimentation comprising subjecting such a variant, e.g. to a simple sandwich binding assay to determine whether or not it binds to an immobilized gp80 or gp130, as described in example 7 of WO 99/02552.

For example, a microtiter 96-well plate (Nunc) is coated with anti-human gp80 monoclonal antibody and 50 ng/ml of gp80 (both from R & D Systems, Minneapolis) is added. After washing in phosphate buffered saline, the IL-6 is added in different wells at different concentrations ranging from 0.1 to 50 ng./ml. After incubation overnight at 40 C, a rabbit polyclonal anti-IL-6 is added, followed by goat antirabbit Ig conjugated with horseradish peroxidase, which is detected by colored reaction (Sigma, St. Louis).

In a preferred embodiment, any such variant has at least 40% identity or homology with the sequence of mature IL-6 or the IL-6R/IL-6 chimeric molecule comprised in WO 99/02552. More preferably, it has at least 50%, at least 60%, at least 70%, at least 80% or, most preferably, at least 90% identity or homology thereto.

Identity reflects a relationship between two or more polypeptide sequences or two or more nucleotide sequences, determined by comparing the sequences. In general, identity refers to an exact nucleotide to nucleotide or amino acid to amino acid correspondence of the two nucleotides or two polypeptide sequences, respectively, over the length of the sequences being compared.

For sequences where there is not an exact correspondence, a "% identity" may be determined. In general, the two sequences to be compared are aligned to give a maximum correlation between the sequences. This may include inserting "gaps" in either one or both sequences; to enhance the degree of alignment. A % identity may be determined over the whole length of each of the sequences being compared (so-called global alignment), that is particularly suitable for sequences of the same or very similar length, or over shorter, defined lengths (so-called local alignment), that is more suitable for sequences of unequal length.

Methods for comparing the identity and homology of two or more sequences are well known in the art. Thus for instance, programs available in the Wisconsin Sequence Analysis Package, version 9.1 (Devereux J et al. 1984), for example the programs BESTFIT and GAP, may be used to determine the % identity between two nucleotides and the % identity and the % homology between two polypeptide sequences. BESTFIT uses the "local homology" algorithm of Smith and Waterman (1981) and finds the best single region of similarity between two sequences. Other programs for determining identity and/or similarity between sequences are also known in the art, for instance the BLAST family of programs (Altschul S F et al, 1990, Altschul S F et al, 1997, accessible through the home page of the NCBI at www.ncbi.nlm.nih.gov) and FASTA (Pearson W R, 1990; Pearson 1988).

Variants of IL-6 or IL-6R/IL-6, which can be used in accordance with the present invention, or nucleic acid coding therefore, include a finite set of substantially corresponding sequences as substitution peptides or nucleotides which can be routinely obtained by one of ordinary skill in the art, without undue experimentation, based on the teachings and guidance presented herein.

Preferred changes for variants in accordance with the present invention are what are known as "conservative" substitutions. Conservative amino acid substitutions of IL-6 or IL-6R/IL-6 may include synonymous amino acids within a group which have sufficiently similar physicochemical properties that substitution between members of the group will preserve the biological function of the molecule (Grantham, 1974). It is clear that insertions and deletions of amino acids may also be made in the above-defined sequences without altering their function, particularly if the insertions or deletions only involve a few amino acids, e.g. under thirty, and preferably under ten, and do not remove or displace amino acids which are critical to a functional conformation, e.g. cysteine residues. Proteins and variants thereof produced by such deletions and/or insertions come within the purview of the present invention.

Preferably, the synonymous amino acid groups are those defined in Table 1. More preferably, the synonymous amino acid groups are those defined in Table 2; and most preferably the synonymous amino acid groups are those defined in Table 3.

TABLE 1

Preferred Groups of Synonymous Amino Acids

| Amino Acid | Synonymous Group |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, Thr, Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, Thr, Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, Thr, Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

TABLE 2

More Preferred Groups of Synonymous Amino Acids

| Amino Acid | Synonymous Group |
|---|---|
| Ser | Ser |
| Arg | His, Lys, Arg |
| Leu | Leu, Ile, Phe, Met |
| Pro | Ala, Pro |
| Thr | Thr |
| Ala | Pro, Ala |
| Val | Val, Met, Ile |
| Gly | Gly |
| Ile | Ile, Met, Phe, Val, Leu |
| Phe | Met, Tyr, Ile, Leu, Phe |
| Tyr | Phe, Tyr |
| Cys | Cys, Ser |
| His | His, Gln, Arg |
| Gln | Glu, Gln, His |
| Asn | Asp, Asn |
| Lys | Lys, Arg |
| Asp | Asp, Asn |
| Glu | Glu, Gln |
| Met | Met, Phe, Ile, Val, Leu |
| Trp | Trp |

TABLE 3

Most Preferred Groups of Synonymous Amino Acids

| Amino Acid | Synonymous Group |
|---|---|
| Ser | Ser |
| Arg | Arg |
| Leu | Leu, Ile, Met |
| Pro | Pro |

TABLE 3-continued

Most Preferred Groups of Synonymous Amino Acids

| Amino Acid | Synonymous Group |
|---|---|
| Thr | Thr |
| Ala | Ala |
| Val | Val |
| Gly | Gly |
| Ile | Ile, Met, Leu |
| Phe | Phe |
| Tyr | Tyr |
| Cys | Cys, Ser |
| His | His |
| Gln | Gln |
| Asn | Asn |
| Lys | Lys |
| Asp | Asp |
| Glu | Glu |
| Met | Met, Ile, Leu |
| Trp | Met |

Examples of production of amino acid substitutions in proteins which can be used for obtaining muteins of IL-6 or IL-6R/IL-6, for use in the present invention include any known method steps, such as presented in U.S. Pat. Nos. 4,959,314, 4,588,585 and 4,737,462, to Mark et al; 5,116,943 to Koths et al., 4,965,195 to Namen et al; 4,879,111 to Chong et al; and 5,017,691 to Lee et al; and lysine substituted proteins presented in U.S. Pat. No. 4,904,584 (Shaw et al).

Specific variants of IL-6, which are useful in connection with the present invention, have been described (WO9403492A1). Furthermore, EP667872B1 describes mutant IL-6 with improved biological activity over wild type IL-6. In addition to this, EP656117B1 describes methods to isolate superagonists of IL-6. The mutants or superagonists may be used according to the invention.

The term "fused protein" refers to a polypeptide comprising IL-6 or an IL-6R/IL-6, or a variant or fragment thereof, fused with another protein, which, e.g. has an extended residence time in body fluids. IL-6 or an IL-6R/IL-6, may thus be fused to another protein, polypeptide or the like, e.g. an immunoglobulin or a fragment thereof.

"Functional derivatives" as used herein cover derivatives of IL-6 or IL-612/IL-6, and their variants and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of IL-6 or IL-6R/IL-6, and do not confer toxic properties on compositions containing it.

These derivatives may, for example, include polyethylene glycol side-chains, which may mask antigenic sites and extend the residence of an IL-6R/IL-6 in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocyclic aroyl groups) or O-acyl derivatives of free hydroxyl groups (for example that of seryl or threonyl residues) formed with acyl moieties.

A "fragment" according to the present invention may e.g. be an active fraction of IL-6 or IL-6R/IL-6. The term fragment refers to any subset of the molecule, that is, a shorter peptide, which retains the desired biological activity, i.e. which has agonistic activity of gp130. Fragments may readily be prepared by removing amino acids from either end of the IL-6 or IL-6R/IL-6 molecule and testing the resultant fragment for its properties to bind to gp80 or gp130, respectively. Proteases for removing one amino acid at a time from either the N-terminal or the C-terminal of a polypeptide are known in the art, and so determining fragments, which retain the desired biological activity, involves purely routine experimentation.

As fragments of IL-6 or an IL-6R/IL-6, variants and fused proteins thereof, the present invention further covers any fragment or precursors of the polypeptide chain of the protein molecule alone or together with associated molecules or residues linked thereto, e.g. sugar or phosphate residues, or aggregates of the protein molecule or the sugar residues by themselves, provided said fraction has agonistic activity on gp130, and in particular on gp130.

The term "salts" herein refers to both salts of carboxyl groups and to acid addition salts of amino groups of the IL-6 or an IL-6R/IL-6 molecule or analogs thereof. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids, such as, for example, hydrochloric acid or sulfuric acid, and salts with organic acids, such as, for example, acetic acid or oxalic acid. Of course, any such salt must retain the biological activity of IL-6 or IL-6R/IL-6, i.e., the ability to activate signaling through gp130.

In a preferred embodiment of the invention, the IL-6 or fragment, variant, fusion protein or salt thereof of the invention is glycosylated at one or more sites.

A glycosylated form of an IL-6R/IL-6 has been described in WO 99/02552 (PCT/IL98/00321), which is the chimeric molecule highly preferred according to the invention. The IL-6R/IL-6 described therein is a recombinant glycoprotein, which was obtained fusing the entire coding sequence of the naturally occurring soluble IL-6 receptor δ-Val (Novick et al., 1990) to the entire coding sequence of mature naturally occurring IL-6, both from human origin. The person skilled in the art will appreciate that glycosylated IL-6 can be produced by recombinant means as well, i.e. by expression in eukaryotic expression systems.

In accordance with the present invention, agonist may be produced in any adequate eukaryotic or procaryotic cell type, like yeast cells, insect cells, bacteria, and the like. It is preferably produced in mammalian cells, most preferably in genetically engineered CHO cells as described for IL-6R/IL-6 in WO 99/02552. Whilst the protein from human origin is preferred, it will be appreciated by the person skilled in the art that a similar fusion protein of any other origin may be used according to the invention, as long as it retains the biological activity described herein.

In a further embodiment of the invention, the IL-6 or fragment, variant, fusion protein or salt thereof of the invention is not glycosylated. Advantageously, the chimeric molecule can then be produced in bacterial cells, which are not capable of synthesizing glycosyl residues, but usually have a high yield of produced recombinant protein. The production of non-glycosylated IL-6 has been described in detail in EP504751B1, for example.

In yet a further embodiment, the IL-6 or fragment, variant, fusion protein or salt thereof of the invention comprises an immunoglobulin fusion, i.e. the molecules according to the invention are fused to all or a portion of an immunoglobulin, and in particular to an Fc fragment of an immunoglobulin.

Methods for making immunoglobulin fusion proteins are well known in the art, such as the ones described in WO 01/03737, for example. The person skilled in the art will understand that the resulting fusion protein of the invention retains the biological activity of IL-6 or IL-6R/IL-6, i.e. the stimulation of gp130 signaling. The resulting fusion protein ideally has improved properties, such as an extended residence time in body fluids (half-life), increased specific activity, increased expression level, or facilitated purification of the fusion protein.

Preferably, the IL-6 or fragment, variant, fusion protein or salt thereof of the invention is fused to the constant region of an Ig molecule. It may be fused to heavy chain regions, like the CH2 and CH3 domains of human IgG1, for example. Other isoforms of Ig molecules are also suitable for the generation of fusion proteins according to the present invention, such as isoforms IgG, or IgG$_4$, or other Ig classes, like IgM or IgA, for example. Fusion proteins may thus be monomeric or multimeric, hetero- or homomultimeric.

Functional derivatives of the IL-6 or fragment, variant, fusion protein or salt thereof of the invention may be conjugated to polymers in order to improve the properties of the protein, such as the stability, half-life, bioavailability, tolerance by the human body, or immunogenicity.

Therefore, a preferred embodiment of the invention relates to a functional derivative of the IL-6 or fragment, variant, fusion protein or salt thereof of the invention comprising at least one moiety attached to one or more functional groups which occur as one or more side chains on the amino acid residues.

A highly preferred embodiment relates to a IL-6 or fragment, variant, fusion protein or salt thereof of the invention linked to Polyethlyeneglycol (PEG). PEGylation may be carried out by known methods, such as the ones described in WO 92/13095, for example.

The use of a vector for inducing and/or enhancing the endogenous production of IL-6, in a cell normally silent for expression of a IL-6, or expressing amounts of IL-6 which are not sufficient, are also contemplated according to the invention. The vector may comprise regulatory sequences functional in the cells desired to express the IL-6. Such regulatory sequences comprise promoters or enhancers. The regulatory sequence is then introduced into the right locus of the genome by homologous recombination, thus operably linking the regulatory sequence with the gene, the expression of which is required to be induced or enhanced. The technology is usually referred to as "endogenous gene activation" (EGA), and it is described e.g. in WO 91/09955.

The substance of the invention may be administered by any adequate route. The subcutaneous route is highly preferred in accordance with the present invention.

The substance of the invention may be delivered to its site of action in any adequate formulation. Preferably, it may be delivered in form of cells expressing and/or secreting IL-6, IL-6R/IL-6, a variant, fused protein or active fraction thereof. As illustrated in the examples below, cells expressing and secreting IL-6R/IL-6 in sufficient amounts have been generated by transfection into the cells using a suitable expression vector.

The invention therefore further relates to the use of a cell expressing the IL-6 or fragment, variant, fusion protein or salt thereof of the invention according to the invention, for manufacture of a medicament for the treatment and/or prevention of microvascular complications. The cells may be administered in any suitable form. However, a polymer-encapsulated IL-6 or an IL-6R/IL-6 expressing, and preferably secreting cell, is a highly preferred mode of delivery of IL-6R/IL-6. The encapsulation procedure is described in detail e.g. by Emerich et al (1994) or U.S. Pat. No. 5,853,385. Suitable cell lines and stable expression systems are well known in the art.

The delivery of the substance according to the invention may also be carried out using a vector, such as an expression vector, comprising the coding sequence of IL-6, an IL-6R/IL-6, a variant, fused protein or fragment thereof. The vector comprises all regulatory sequences needed for expression of the desired protein in the human body, and preferably in peripheral nervous cells. Regulatory sequences for expression vectors are known by the person skilled in the art. The invention thus also relates to the use of a vector comprising the coding sequence of the IL-6 or fragment, variant, fusion protein or salt thereof according to the invention for manufacture of a medicament for the treatment and/or prevention of microvascular complications.

Any expression vector known in the art may be used according to the invention. However, the use of a virally derived gene therapy vector is highly preferred. Use of viral vectors for IL-6 expression are described by Bensadoun et al 2001.

The substance of the invention is preferably administered to the human body as a pharmaceutical composition. The pharmaceutical composition may comprise the IL-6 or fragment, variant, functional derivative, fusion protein or salt thereof of the invention as such, or cell expressing said polypeptide, or an expression vector, in particular a lentiviral gene therapy vector comprising the coding sequence of IL-6, an IL-6R/IL-6 or a variant, fused protein, or active fragment thereof, optionally together with one or more pharmaceutically acceptable carriers, diluents or excipients, for the treatment and/or prevention of microvscular complications.

The definition of "pharmaceutically acceptable" is meant to encompass any carrier, which does not interfere with effectiveness of the biological activity of the active ingredient and that is not toxic to the host to which it is administered. For example, for parenteral administration, the active component may be formulated in a unit dosage form for injection in vehicles such as saline, dextrose solution, serum albumin and Ringer's solution.

The active component can be administered to a patient in a variety of ways. The routes of administration include intradermal, transdermal (e.g. in slow release formulations), intramuscular, intraperitoneal, intravenous, subcutaneous, oral, epidural, topical, and intranasal routes. Any other therapeutically efficacious route of administration can be used, for example absorption through epithelial or endothelial tissues or by gene therapy wherein a DNA molecule is administered to the patient (e.g. via a vector), which causes the active polypeptide to be expressed and secreted in vivo. In addition the active molecule can be administered together with other components of biologically active agents such as pharmaceutically acceptable surfactants, excipients, carriers, diluents and vehicles.

For parenteral (e.g. intravenous, subcutaneous, intramuscular) administration, the active component can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

It is a further object of the present invention to provide for a method for treating and/or preventing microvascular complications, comprising administering to a patient in need thereof an effective amount of the IL-6 or fragment, variant, fusion protein or salt thereof of the invention, optionally together with a pharmaceutically acceptable carrier.

An "effective amount" refers to an amount of the active ingredients that is sufficient to affect the course and the severity of the diseases described above, leading to the reduction or remission of such pathology. The effective amount will depend on the route of administration and the condition of the patient.

The dosage administered, as single or multiple doses, to an individual will vary depending upon a variety of factor, including pharmacokinetic properties, the route of administration, patient conditions and characteristics (sex, age, body weight, health, size), extent of symptoms, concurrent treatments, frequency of treatment and the effect desired. Adjustment and manipulation of established dosage ranges are well within the ability of those skilled.

It should be noted that the active dose of IL-6 as thrombopoietic factor in rodents is above 500 mcg/kg, versus 10 mcg/kg in monkeys (Herodin et al. 1992 Blood 80 (3) 688). Therefore IL-6 appears to be 50 times more effective in primates than in rodents. Therefore hrIL-6 is expected to be 50 times, or one order of magnitude more effective or at least 5 folds more effective in humans than in rodents. Since in the present embodiments, positives results in microvascular complication were found in rodents at doses in the range of 10 to 30 mcg/kg, thus a dose of 50, 10 and/or 5 time less human recombinant IL-6 is expected to be effective for preventing/treating microvascular complications in man. Preferably the IL-6 or fragment, variant, fusion protein or salt thereof of the invention is used at doses of about 2 to 3 mcg/kg, 1 to 3 mcg/kg, and 0.2 to 0.6 mcg/kg.

Alternatively, a fixed low dose of IL-6 can be administrated such in the range 140 to 210, 70 to 210, and 14 to 42 mcg per patient.

In a preferred embodiment of the invention, the IL-6 or fragment, variant, functional derivative, fusion protein or salt thereof of the invention is administered three times per week.

A method for treating microvascular complications, comprising administering to a patient in need thereof an effective amount of a cell expressing IL-6 or an IL-6R/IL-6, or a variant, fused protein, active fraction thereof, is also considered in accordance with the present invention. A method for treating microvascular complications comprising administering to a patient in need thereof an expression vector comprising the coding sequence of IL-6 or an IL-6R/IL-6, a variant, fused protein, or active fraction thereof, is a further objects of the invention.

In a preferred embodiment of the invention, the expression vector is a gene therapy vector. The use of a viral vector, in particular a lentiviral vector, is highly preferred.

The present invention will now be described in more detail in the following non-limiting examples and the accompanying drawings.

Having now fully described this invention, it will be appreciated by those skilled in the art that the same can be performed within a wide range of equivalent parameters, concentrations and conditions without departing from the spirit and scope of the invention and without undue experimentation.

While this invention has been described in connection with specific embodiments thereof, it will be understood that it is capable of further modifications. This application is intended to cover any variations, uses or adaptations of the invention following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

Reference to known method steps, conventional methods steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning an range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

EXAMPLES

Example 1

Effect of IL-6 in Motor and Sensor Deficits in Experimental Diabetes

The aim of the following experiments was to examine whether IL-6 treatment could correct existing abnormalities in large myelinated and small nerve fiber populations in the streptozotocin-diabetic rat model of diabetic neuropathy.

Experimental Set-Up: Diabetic Rat Model and IL-6 Administration Regimen.

Diabetes was induced in mature (19 week old) male Sprague-Dawley rats by a single intraperitoneal (i.p.) injection of streptozotocin (40-45 mg/kg). After 4 weeks without treatment, during which nerve conduction velocity (NCV) and blood flow deficits develop and stabilize [Cameron 1991], diabetic rats were given 4 weeks treatment with IL-6 at 2 doses of 10 mcg/kg and 30 mcg/kg, respectively, sub-cutaneously, and 3-times per week.

Before the start of IL-6 treatment and at the end of the treatment period, tactile allodynia (pain resulting from a non-noxious stimulus to normal skin) and mechanical stimulation thresholds of the foot were measured by an electronic von Frey hair apparatus and the Randall-Sellito test [Randall et al. 1957, Chaplan et al. 1994], respectively. Latencies for withdrawal reflexes to noxious thermal stimulation of the foot were estimated by the Hargreaves plantar test [Hargreaves 1988]. All tests were carried out using commercially available equipment (Ugo-Basile, Comerio, Italy). Briefly, measurements were made in a constant temperature room at the same time each day, and rats were given a 2-day period for familiarization with handling, the environment, equipment, and experimental procedure.

Experimental groups were as follows:
Nondiabetic control (C; n=10)
4 wk diabetes (1D; n=8-10)
8 wk diabetes (2D; n=10)
4 wk diabetes+4 week 10 mcg/kg IL6 (D10; n=10)
4 wk diabetes+4 week 30 mcg/kg IL6 (D30; n=8)

Sciatic motor NCV in the branch to tibialis anterior muscle and saphenous sensory NCV were estimated as previously described [Cameron 1989].

Blood samples for estimation of plasma glucose concentration (GOD-Perid method, Boehringer Mannheim) were taken from the carotid cannula at the end of the experiments.

Data were expressed as group mean±SEM. They were subjected to Bartlett's test for equality of variance and where necessary given a log transformation (vascular conductance) before one way ANOVA. Where overall significance ($p<0.05$) was attained, between-group statistical differences were determined by the Newman-Keuls multiple comparison test.

Experimental Results:

Diabetic rats were hyperglycaemic and lost weight over the course of the experiment, mainly during the first 4 weeks (Table 4). IL-6 treatment did not affect the glycaemic state or body weight loss.

TABLE 4

| Group | n | Body weight (g) Before | After | Plasma glucose (mM) |
|---|---|---|---|---|
| Control | 10 | — | 485 ± 11 | 6.32 ± 0.65 |
| 4 wk Diabetes | 8 | 471 ± 6 | 360 ± 3 | 41.54 ± 1.61 |
| 8 wk Diabetes | 10 | 465 ± 10 | 359 ± 8 | 39.32 ± 2.75 |
| Diabetes + IL-6 10 | 10 | 468 ± 4 | 359 ± 18 | 40.38 ± 4.04 |
| Diabetes + IL-6 30 | 8 | 470 ± 5 | 384 ± 15 | 46.4 ± 3.34 |

Figure 2:
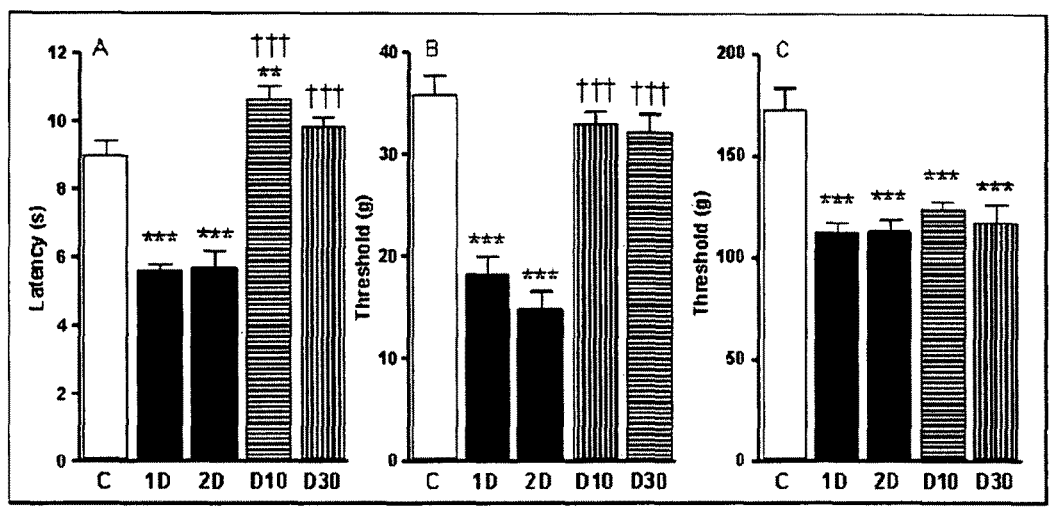
FIG. 2 shows sensory testing thresholds; latency for foot withdrawal to thermal (noxious) stimulation (A), allodynia (pain resulting from a non-noxious stimulus to normal skin) test (B) and mechanical pressure (C). Statistics: one-way ANOVA+Newman-Keuls multiple comparison test;  $p<0.01$, * $p<0.001$ versus control (C) group; ††† $p<0.001$ effects of IL-6 treatment versus diabetic (D) group.

Sciatic motor NCV was 22.4±1.2% (mean±SEM) and 21.7±1.0% reduced ($p<0.001$) after 0.4 and 8 weeks of diabetes, respectively (FIG. 1A, bars 1D and 2D respectively). IL-6 corrected this deficit by 90.9±3.6% (FIG. 1A, D10, 10 mcg/kg; 5, $p<0.001$) and 88.4±6.2% (FIG. 1A, D30, 30 mcg/kg; $p<0.001$). Similarly, sensory saphenous NCV deficits of 17.1±1.3% and 17.8±1.4% after 4 ($p<0.001$) and 8 ($p<0.001$) weeks of diabetes (FIG. 1B), respectively, were completely corrected ($p<0.001$) by both IL-6 doses. The latency for foot withdrawal from a noxious thermal stimulus was reduced ($p<0.001$) by 37.8±2.1% after 4 weeks and 37.0±5.5% after 8 weeks of diabetes (FIG. 2A), indicating thermal hyperalgesia, which was completely rectified ($p<0.001$) by both IL-6 doses. In fact, for the 10 mcg/kg dose, response latencies were supernormal ($p<0.01$). Thresholds for foot withdrawal to tactile stimulation by an electronic von Frey hair apparatus were decreased by 49.1±4.8% ($p<0.001$) and 58.7±4.9% ($p<0.001$) after 4 and 8 weeks of diabetes, respectively (FIG. 2B). IL-6 treatment corrected this tactile allodynia by 83.9±6.7% (10 mcg/kg; $p<0.001$) and 79.3±10.3% (30 mcg/kg; $p<0.001$). In response to a slowly ramped increase in mechanical pressure, diabetic rats showed an approximately 35% ($p<0.001$) reduction in thresholds for foot withdrawal, indicating mechanical hyperalgesia (FIG. 2C). However, in contrast to the other pain-related measures, this appears slightly affected or not affected by IL-6 treatment.

The data clearly show that IL-6 at both doses used (10 and 30 mcg/kg thrice weekly) completely corrected sciatic motor and saphenous sensory NCV deficits in experimental diabetes.

IL-6 treatment corrected aspects of large and small fibre dysfunction in diabetic rats, including motor and sensory conduction velocity such as thermal hyperalgesia and tactile allodynia.

Example 2

Beneficial Effect of IL-6 in Microvascular Complications

There is indirect evidence that diabetic neuropathy results from hypoxia and reduced blood flow (Cameron 2001). In the animal model illustrated in Example 1, there is shown impairment in neural performance in a model of diabetes. In Example 1. It is also shown that neural performance is corrected by IL-6.

The following experiments were carried out to directly asses whether neuropathy in the diabetes model of example 1 mimics the human disease in terms of neural blood flow defficiency, and whether the beneficial effects of IL-6 in this model is due to correction of neural blood flow.

Thus, the blood flow in endoneural tissue and the changes in systemic blood pressure were measured in non treated rats versus diabetic rats, and in diabetic rats treated with IL-6.

The rats of Example 1 were anaesthetized with thiobutabarbital (50-100 mcg/kg i.p.) and the carotid artery and trachea (macrovasculature) were cannulated for blood pressure measurements and artificial respiration, respectively.

Sciatic endoneurial nutritive (capillary) blood flow was measured by microelectrode polarography and hydrogen clearance as previously described [Cameron 1991].

Briefly, sciatic endoneurial blood flow was estimated in the limb contralateral to that for conduction velocity measurements by microelectrode polarography and hydrogen clearance [Cameron 1991, Chaplan 1994 and Randall 1957]. Rats were artificially ventilated. The carotid artery was cannulated to monitor blood pressure, and when necessary, rats were given neuromuscular blockade using d-tubocurarine (2 mg kg-1 via the carotid cannula) to reduce mechanical movement artifacts. The level of anaesthesia was monitored by observing any reaction of blood pressure to manipulation, and supplementary thiobutabarbital anaesthetic was given as necessary. The sciatic nerve was exposed and the skin around the incision sutured to a metal ring to form a pool filled with mineral oil at 37° C. During recordings, pool temperature was maintained at 35-37° C. by radiant heat. A glass-insulated platinum microelectrode, polarized at 250 mV with respect to a subcutaneous reference electrode, was inserted into the sciatic nerve endoneurium between the sciatic notch and the nerve trifurcation above the knee. 10% H2 was added to the inspired gas, the proportions of 02 and N2 was adjusted to 20% and 70% respectively. When the H2 current recorded by the electrode had stabilized, indicating equilibrium with arterial blood, the H2 supply was shut off and N2 delivery was increased appropriately. H2 clearance was recorded until a stable baseline was reached, which was defined as no systematic decline in electrode current over 5 min. This procedure was then repeated at another nerve site. After the experiment, clearance curves were digitized and mono- or bi-exponen-tial curves fitted to the data by computer using non-linear regression analysis (Prism, Graphpad, San Diego, Calif., USA) and the general bi-exponential equation:

$$y = a\exp(-bx) + c\exp(-dx) + e$$

Where y is the electrode hydrogen current (arbitrary units), x is time (min), a and c are weighting constants for fast (non-nutritive) and slow (nutritive) clearance components respectively, b is the fast component and d is the slow component (ml min-1 ml nerve-1), and e is the baseline electrode current (arbitrary units). Assuming a tissue density of 1, nutritive blood flow was calculated as $d \times 100$ (ml min-1 100 g-1). Vascular conductance was calculated by dividing blood flow by the mean arterial blood pressure over the recording period for that particular clearance curve. The averages from the two determinations were taken to represent sciatic endoneurial blood flow parameters.

Figure 3:
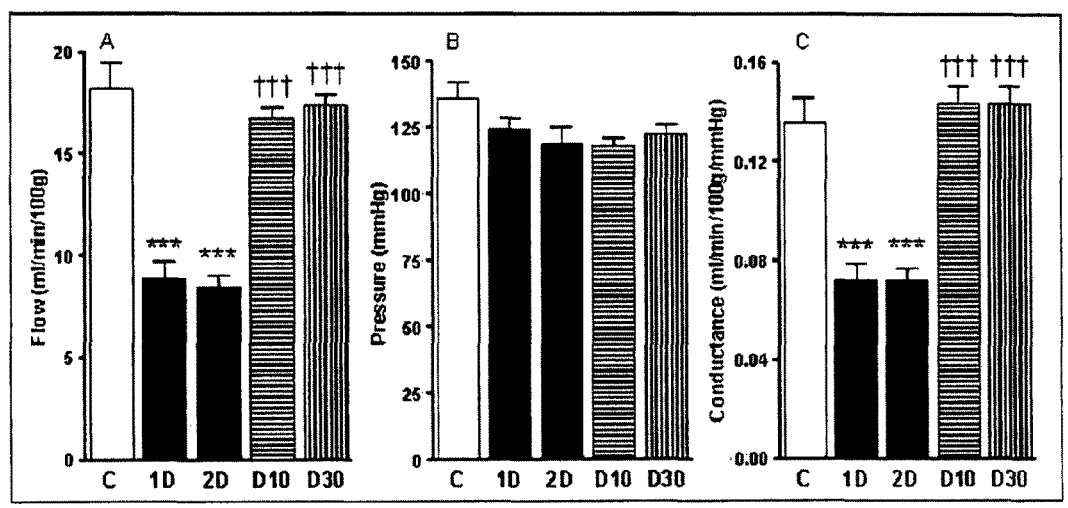
FIG. 3 shows siatic nutritive (capillary) endoneurial blood flow (A), mean systemic blood pressure (B) and endoneurial vascular conductance (C). Statistics: one-way ANOVA+ Newman-Keuls multiple comparison test; *** $p<0.001$ versus control (C) group; ††† $p<0.001$ effects of IL-6 treatment versus diabetic (D) group.

The results summarized in FIG. 3A show that sciatic endoneurial nutritive (capillary) perfusion was $51.3 \pm 4.2\%$ and $53.6 \pm 2.7\%$ decreased ($p<0.001$) by 4 and 8 weeks of diabetes (FIG. 3A). IL-6 treatment corrected this flow deficit by $84.3 \pm 5.2\%$ (10 mcg/kg; $p<0.001$) and $90.8 \pm 5.3\%$ (30 mcg/kg; $p<0.001$), such that vascular conductance values were in the top half of the non-diabetic range (FIG. 3C). There were no significant differences in mean systemic blood pressure (FIG. 3B) between groups. The results are summarized in Table 5.

Thus, IL-6 had marked vascular effects in improving sciatic endoneurial nutritive flow. Overall, IL-6 performed very well in reversing the microvascular defects.

TABLE 5

| Group | MNCV (m/s) | SNCV (m/s) | Flow (ml/min/100 g) | Pressure (mm Hg) | Conductance (ml/min/100 g/mmHg) | Thermal (s) | Allodynia (g) | Mechanical (g) |
|---|---|---|---|---|---|---|---|---|
| C | 65.13 ± 0.74 | 60.19 ± 0.69 | 18.24 ± 1.19 | 136.1 ± 5.6 | 0.136 ± 0.010 | 8.99 ± 0.40 | 35.78 ± 1.90 | 172.4 ± 10.6 |
| 4 wk D1 | 50.53 ± 0.70 | 49.98 ± 0.80 | 8.89 ± 0.77 | 124.6 ± 3.7 | 0.072 ± 0.007 | 5.59 ± 0.19 | 18.22 ± 1.71 | 111.9 ± 4.8 |
| 8 wk D2 | 50.97 ± 0.62 | 49.45 ± 0.82 | 8.47 ± 0.50 | 118.6 ± 6.4 | 0.073 ± 0.004 | 5.66 ± 0.49 | 14.77 ± 1.75 | 112.7 ± 5.6 |
| DL10 | 63.80 ± 0.53 | 61.12 ± 0.72 | 16.77 ± 0.49 | 118.0 ± 2.7 | 0.144 ± 0.007 | 10.65 ± 0.33 | 32.96 ± 1.18 | 123.5 ± 3.6 |
| DL30 | 63.43 ± 0.91 | 60.28 ± 0.58 | 17.38 ± 0.50 | 122.6 ± 3.3 | 0.144 ± 0.007 | 9.82 ± 0.27 | 32.14 ± 1.80 | 117.2 ± 8.5 |

Example 3

Production of IL-6 an IL-6R/IL-6 in CHO Cells

The cDNA sequence encoding for the soluble IL-6 receptor (natural form of sIL-6R found in urine, Oh et al., 1997) is fused with that encoding for mature IL-6. Sequences for 3 bridging amino acids (EFM) were also present. The fused gene is inserted in an expression vector under the control of CMV promoter and introduced into CHO cells. A production process is developed and the resulting recombinant protein is purified by immunopurification using an anti-IL-6R monoclonal antibody. FIG. 4 schematically shows the composition of the IL-6R/IL-6. The mature protein comprises 524 amino acids. A protein produced and purified as outlined above is suitable to be administered according to the invention.

Recombinant human IL-6 (r-hIL-6) was produced in genetically engineered Chinese Hamster Ovary (CHO) cells. The production process begun with the growth and expansion of cells from a working cell bank (WCB) and continued under conditions where r-hIL-6 is secreted into the culture medium. The r-hIL-6 was harvested and purified from culture medium of the engineered cells. Purity was above 99.6% and potency 23.3×106 IU/ml (based on a Hybridoma growth factor (HGF) activity of IL-6 of Van Damme J, Van Snick J. Dev Biol Stand. 1988;69:31-8).

REFERENCES

Altschul S F et al, J Mol Biol, 215, 403-410, 1990
Altschul S F et al, Nucleic Acids Res., 25:389-3402, 1997
Baudry et al. Am J. Physiol. 1996 271 (3 Pt 2): H1186-92. 1996.
Bensadoun, Almeida, Dreano, Aebischer and Deglon. European Journal of Neuroscience Vol. 14 1753-1761. 2001.
Boulton A J M 1997 In: Pickup J U Williams G (eds) Textbook of Diabetes. $2^{nd}$ edn. Blackwell, Oxford pp 58.1-58.20.
Chebath, J., Fischer, D., Kumar, A., Oh, J. W., Kollet, 0., Lapidot, T., Fischer, M., Rose-John, S., Nagler, A., Slavin, S. and Revel, M. Eur. Cytokine Netw. 1997 8,359-365.
Cameron N E, Eaton S E M, Cotter M A, Tesfaye S (2001) Vascular factors and metabolic interactions in the pathogenesis of diabetic neuropathy. Diabetologia 44:1973-1988
Cameron N E, Cotter M A, Robertson S (1989) The effect of aldose reductase inhibition on the pattern of nerve conduction deficits in diabetic rats. Q J Exp Physiol 74: 917-926
Cameron N E, Cotter M A, Low P A (1991) Nerve blood flow in early experimental diabetes in rats: relation to conduction deficits. Am J Physiol 261: E1-E8.
Chaplan S R, Bach F W, Pogrel J W, Chung J M, Yaksh T L (1994) Quantitative assessment of tactile allodynia in the rat paw. J Neurosci Meth 53:55-63
Chebath et al, Eur Cytokine Netw. (Kollet et al, Blood. 1999 Aug. 1; 94(3): 923-31).
Chebath et al. Eur Cytokine Netw. 1997 December; 8(4):359-65.).
Corbi et al 2000 Eur J Cardiotherac Surg. 18 (1):98-103
Devereux J et al, Nucleic Acids Res, 12, 387-395, 1984.
Disthabanchong et al. Clin Nephrol. 2002 October; 58(4):289-95).
Dyck et al. PNAS 82: 2513-7 1985.
Emerich D F, Cain C K, Greco C, Saydoff J A, Hu Z Y, Liu H, Lindner M D Cell Transplant. 1997 May-June; 6(3):249-66.
Emerich, D. F., Lindner, M. D., Winn, S. R., Chen, E.-Y., Frydel, B. R., and Kordower, J. H. (1996). J. Neurosci., 16, 5168-5181.
Emerich D F, Winn S R, Hantraye P M, Peschanski M, Chen E Y, Chu Y, McDermott P, Baetge E E, Kordower J H Nature. 1997 Mar. 27; 386(6623):395-9.
Emerich D F, Hammang J P, Baetge E E, Winn S R Exp Neurol. 1994 November; 130(1):141-50.
Fisher et al., J. Neuroimmunology 119 (2001) 1-9
Frei et al., J. Neuroimmunol., 31:147 (1991)
Gadient and Otten, 1997, Mendel et al, 1998
Halimi H, Eisenstein M, Oh J, Revel M and Chebath J. Eur. Cytokine Netw. 1995, 6: 135-143,
Hargreaves K, Dubner R, Brown F, Flores C, Joris J (1988) A new and sensitive method for measuring thermal nociception in cutaneous hyperalgesia. Pain 32:77-88.
Herodin et al. 1992 Blood 80 (3) 688
Hirano et al, 1986 Nature (London) 234-73 (1986)
Hirano T, Matsuda T and Nakajima K: Stem cells 1994, 12:262-277.
Hirota H, Kiyama H, Kishimoto T, Taga T J Exp Med. 1996 Jun. 1; 183(6):2627-34.
Jude 1999 Diabetes Rev 7:395-410.
Kado et al. 1999 Acta Diabetol. June 36 (1-2)67-72
Kollet et al, Blood. 1999 Aug. 1; 94(3):923-31
Masson Diabetologia. 1988 October; 31(10):762-5.
Minghini et al. Shock Mar; 9(3):210-51998.
May et al, Proc Natl Acad Sci USA 83:8957 (1986);
Mendel, I., Katz, A., Kozak, N., Ben-Nun, A. and Revel, M. Eur. J. Immunol. 1998 28, 1727-1737.
Murakami M, Hibi M, Nakagawa N, Nakagawa T, Yasukawa K, Yamanishi K, Taga T,
Kishimoto T Science. 1993 Jun. 18; 260(5115):1808-10.
Novick, D., Shulman, L. M., Chen, L. and Revel, M. Cytokine 1992 4, 6-11.
Novick D, Shulman L M, Chen L and Revel M. Cytokine 1992, 4: 6-11.
Novick D. Engelmann H. Wallach D. Leitner O. Revel M. Rubinstein M. Journal of Chromatography 1990. 510:331-7.
Paonessa G, Graziani R, Deserio A, Savino R, Ciapponi L, Lahmm A, Salvati A L, Pearson W R, Methods in Enzymology, 183, 63-99, 1990
Pearson W R and Lipman D J, Proc Nat Acad Sci USA, 85, 2444-2448,1988
Rudas B. Streptozotocin. Azrneimittel-Forschung, 22, 830-861. (1972)
Randall L O, Sellito J J (1957) A method for measurement of analgesic activity on inflamed tissue. Arch Int Pharmacodyn Ther 111:409-419
Skundric D S, Lisak R P (2003) Role of neuropoietic cytokines in development and progression of diabetic polyneuropathy: from glucose metabolism to neurodegeneration. Exp Diabesity Res 4:303-12
Smith and Waterman J Mol Biol, 147,195-197, 1981, Advances in Applied Mathematics, 2, 482-489, 1981.
Taga, T., Hibin M., Hirata, Y., Yamasaki, K., Yasukawa, K., Matsuda, T., Hirano, T. and Kishimoto, T. Cell 1989 58, 573-581.
Toulmond, S., Vige, X., Fage, D., and Benavides, J. Neurosci Lett 1992, 144, 49-52.
Ward L D, Howlett G J, Discolo G, Yasukawa K, Hammacher A, Moritz R L and Simpson R J. High affinity interleukin-6 receptor is a hexameric complex consisting of two molecules each of interleukin-6, interleukin-6 receptor and gp130. J. Biol. Chem. 1994, 269: 23286-23289.
Yamada, M., and Hatanaka, H.: Brain Res 1994, 643, 173-80.
Zilberstein et al, EMKO J 5:2529 (1986)

The invention claimed is:

1. A method for inhibiting or reducing a microvascular complication selected from the group consisting of diabetic retinopathy, diabetic nephropathy and diabetes-independent peripheral neuropathy, comprising administering to a patient in need thereof an effective amount of IL-6, soluble IL-6R/IL-6 chimera, or a fusion protein comprising IL-6 and an immunoglobulin (Ig), or salt thereof, optionally together with a pharmaceutically acceptable carrier, to inhibit or to reduce the microvascular complication, with the proviso that the microvascular complication is not diabetic neuropathy.

2. A method according to claim 1, wherein IL-6 is administered by subcutaneous route.

3. The method according to claim 1, wherein the microvascular complication is diabetic retinopathy.

4. The method according to claim 1, wherein the microvascular complication is diabetic nephropathy.

5. The method according to claim 1, wherein the microvascular complication is diabetes-independent peripheral neuropathy and is due to chronic hypoxia.

6. The method according to claim 1, wherein the microvascular complication is diabetes-independent peripheral neuropathy and is due to chronic obstructive pulmonary disease.

7. The method according to claim 1, wherein the microvascular complication is accompanied by hypertension.

8. The method according to claim 1, wherein the microvascular complication is accompanied by ulcer.

9. The method according to claim 1, wherein the IL-6 administered is recombinant.

10. The method according to claim 1, wherein soluble IL-6R/IL-6 chimera is administered.

11. The method according to claim 1, wherein the IL-6 administered is glycosylated at one or more sites.

12. The method according to claim 1, wherein the IL-6 administered is not glycosylated.

13. The method according to claim 1, wherein a fusion protein comprising IL-6 and an immunoglobulin is administered.

14. The method according to claim 1, wherein the effective amount of IL-6, soluble IL-6R/IL-6 chimera, or a fusion protein comprising IL-6 and an immunoglobulin (Ig) is selected from the range of about 2 to 3 mcg/kg, 1 to 3 mcg/kg, and 0.2 to 0.6 mcg/kg.

15. The method according to claim 1, wherein the effective amount is selected from about 3 mcg/kg, 2 mcg/kg, 1 mcg/kg, 0.6 mcg/kg and 0.2 mcg/kg.

16. The method according to claim 1, wherein the effective amount is selected from the range of 140 to 210, 70 to 210, and 14 to 42 mcg per patient.

17. The method according to claim 1, wherein the IL-6 is administered three times per week.

* * * * *